United States Patent [19]

Das

[11] Patent Number: 4,521,539
[45] Date of Patent: Jun. 4, 1985

[54] TETRAHYDROFURANYL SUBSTITUTED ETHERS

[75] Inventor: Jagabandhu Das, Plainsboro, N.J.

[73] Assignee: E. R. Squibb & Sons, Inc., Princeton, N.J.

[21] Appl. No.: 609,054

[22] Filed: May 10, 1984

[51] Int. Cl.$^3$ .................... A61K 31/34; C07D 307/16
[52] U.S. Cl. .................... 514/461; 549/214; 549/365; 549/448; 549/462; 549/498; 549/501; 549/502
[58] Field of Search .................... 549/501; 424/285

[56] References Cited

U.S. PATENT DOCUMENTS

| | | | |
|---|---|---|---|
| 4,061,643 | 12/1977 | Cragoe et al. | 549/501 X |
| 4,143,054 | 3/1979 | Sprague | 549/463 |
| 4,172,839 | 10/1979 | Wissner | 549/501 X |
| 4,187,236 | 2/1980 | Sprague | 549/463 |
| 4,220,594 | 9/1980 | Sprague | 549/386 |
| 4,228,180 | 10/1980 | Sprague | 549/463 |
| 4,254,044 | 3/1981 | Sprague | 549/463 |
| 4,440,781 | 4/1984 | Benecke et al. | 549/501 X |

FOREIGN PATENT DOCUMENTS 0043292 8/1982 European Pat. Off. .
2039909 8/1980 United Kingdom .

OTHER PUBLICATIONS

"Prostaglandin Synthesis", Bindra et al., Academic Press Inc. (1977), pp. 482–489.

*Primary Examiner*—Richard L. Raymond
*Attorney, Agent, or Firm*—Lawrence S. Levinson; Burton Rodney

[57] ABSTRACT

Tetrahydrofuranyl substituted ethers are provided having the structural formula

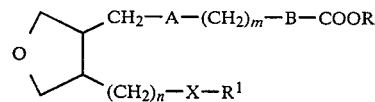

wherein A is $(CH_2)_2$, $CH=CH$ or a single bond, m is 1 to 5, B is a single bond or $CH=CH$, n is 1 to 4, X is O or

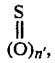

wherein n' is 0, 1 or 2, R is H, lower alkyl or alkali metal and $R^1$ is lower alkyl, arylalkyl, aryl, cycloalkyl, cycloalkylalkyl or lower alkenyl and including all stereoisomers thereof.

The compounds are cardiovascular agents useful, for example, in the treatment of thrombolytic disease and as antiinflammatory agents and analgesics.

19 Claims, No Drawings

TETRAHYDROFURANYL SUBSTITUTED ETHERS

DESCRIPTION OF THE INVENTION

The present invention relates to tetrahydrofuranyl substituted ethers which are cardiovascular agents useful, for example, in the treatment of thrombolytic disease. These compounds have the general formula

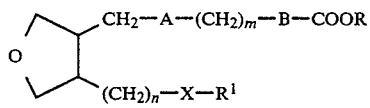

(including all stereoisomers thereof) wherein A is $-(CH_2)_2-$, $-CH=CH-$ or a single bond; m is 1 to 8; B is a single bond or $-CH=CH-$; R is H, lower alkyl or alkali metal; n is 1 to 4, X is $-O-$ or

wherein n' is 0, 1 or 2; and $R^1$ is lower alkyl, arylalkyl, aryl, cycloalkyl, cycloalkylalkyl or lower alkenyl.

The term "lower alkyl" or "alkyl" as employed herein includes both straight and branched chain radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or $CF_3$, an alkoxy substituent, an aryl substituent (for example,

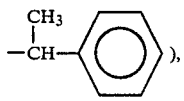

an alkyl-aryl substituent, a haloaryl substituent, a cycloalkyl substituent or an alkylcycloalkyl substituent.

The term "cycloalkyl" includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups and/or lower alkoxy groups.

The term "aryl" or "Ar" as employed herein refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be lower alkyl, halogen (Cl, Br or F), or lower alkoxy.

The term "lower alkenyl" or "alkenyl" includes straight or branched chain radicals of from 2 to 12 carbons, preferably 2 to 6 carbons in the normal chain, which include one double bond in the normal chain, such as 2-propenyl, 3-butenyl, 2-butenyl, 1-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl and the like.

The term "aralkyl", "aryl-alkyl" or "aryl-lower alkyl" as used herein refers to lower alkyl groups as discussed above having an aryl substituent, such as benzyl or methylbenzyl

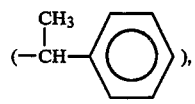

The term "cycloalkylalkyl" as used herein refers to cycloalkyl groups as defined above linked to an alkyl group as defined above.

The term "lower alkoxy", "alkoxy" or "aralkoxy" includes any of the above lower alkyl, alkyl or aralkyl groups linked to an oxygen atom.

The term "halogen" or "halo" as used herein refers to chlorine, bromine, fluorine or iodine with chlorine being preferred.

The term "$(CH_2)_m$", $(CH_2)_n$, and "$(CH_2)_2$" includes straight or branched chain radicals having from 1 to 8 carbons and 1 to 4 carbons in the normal chain in he case of $(CH_2)_m$, and $(CH_2)_n$, respectively, and 2 carbons in the normal chain in the case of $(CH_2)_2$, and may contain one or more lower alkyl substituents. Examples of $(CH_2)_m$, $(CH_2)_n$ and $(CH_2)_2$ groups include

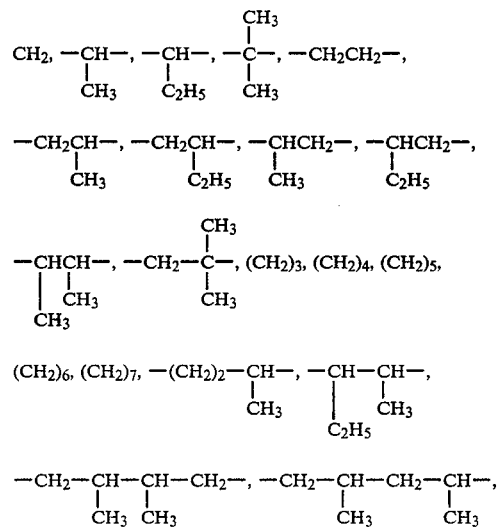

and the like.

Preferred are those compounds of formula I wherein A is $-CH=CH-$ or $-(CH_2)_2-$, B is a single bond, m is 2 or 5, n is 1 or 2, R is hydrogen and $R^1$ is lower alkyl, phenyl, cycloalkyl or benzyl.

Compounds of formula I of the invention of the cis series may be prepared using aldehyde II as the starting material

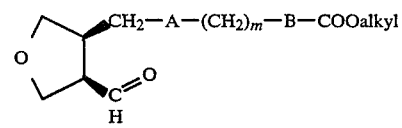

Thus, to prepare compounds of formula I wherein X is O, B is a single bond, A is $CH=CH$ or $(CH_2)_2$ and n is 1, aldehyde II is reduced by treating II with a reducing agent such as sodium borohydride, or sodium cyanoborohydride in an inert organic solvent, such as methanol, to form alcohol III

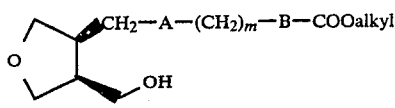

Alcohol III is then made to undergo ether formation by reacting III with a compound of the structure IV

Y—R¹  IV wherein Y is Cl, Br, I

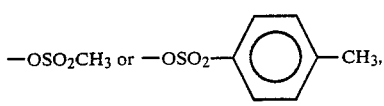

in the presence of potassium hydroxide or other strong base and an inert organic solvent such as xylene, tetrahydrofuran (THF), dimethylsulfoxide (DMSO) or dimethylformamide (DMF) employing a molar ratio of III:IV of within the range of from about 0.2:1 to about 0.1:1, to form V

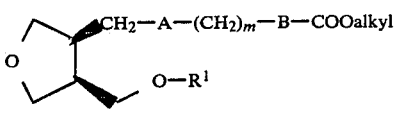

Where in formula IV, X is Br or Cl, a phase transfer etherification is employed in which case THF is used as the solvent and a transfer reagent such as (C₄H₉)₄NHSO₄ or (C₆H₅CH₂)(CH₃)₂NHSO₄ is employed.

The ester V may then be hydrolyzed by treatment with a strong base such as lithium hydroxide, potassium carbonate or sodium hydroxide in the presence of an inert organic solvent such as tetrahydrofuran to form the corresponding alkali metal salt which is treated with a strong acid, such as HCl, to form the cis compounds of the invention

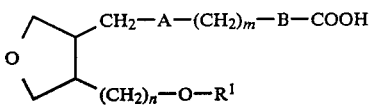

Compounds of formula I of the invention of the trans series wherein X is O, and B is a single bond, may be prepared using aldehyde IIA

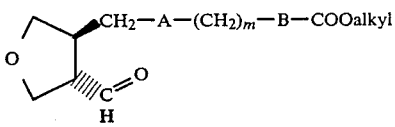

which itself is prepared from aldehyde II by simply subjecting II to an epimerization reaction wherein II is reacted with sodium methoxide in the presence of methanol to form aldehyde IIA.

Aldehyde IIA is then reduced by treatment with sodium borohydride or sodium cyanoborohydride in the presence of an inert organic solvent such as methanol to form alcohol VI

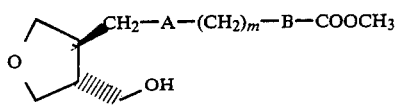

which is then etherified by reaction with a mesylate, tosylate or halide IV

Y—R¹  IV as described above with respect to the cis series to form ester VII

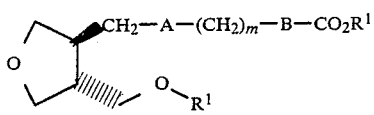

Ester VII is then hydrolyzed by treatment with a strong base such as lithium hydroxide, potassium carbonate or sodium hydroxide in the presence of an inert organic solvent such as tetrahydrofuran, to form the corresponding alkali metal salt which is treated with a strong acid, such as HCl, to form the trans compounds of the invention VIII

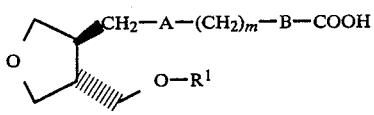

Compounds of the invention wherein X is S may be prepared from hydroxymethyl compound III or VI. Thus, where A is —CH=CH— and B is a single bond, compound III or VI is subjected to a tosylation reaction, for example, by reacting III or VI with tosyl chloride in pyridine to form tosylate IX

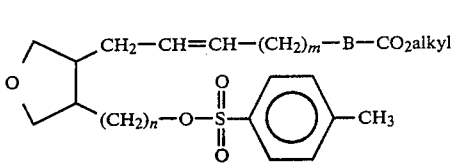

To form the tosylate IXA (where A is (CH₂)₂, compound III or VI is reduced, for example, with hydrogen over a palladium on carbon catalyst, to form hydroxymethyl compound IIIA or VIA (where A is (CH₂)₂)

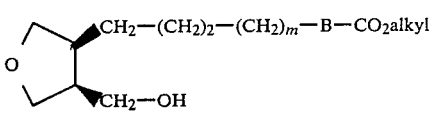

or

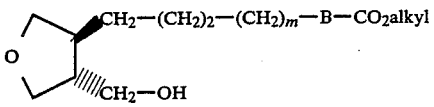

Compound IIIA or VIA is subjected to a tosylation reaction to form tosylate IXA (where A is (CH₂)₂)

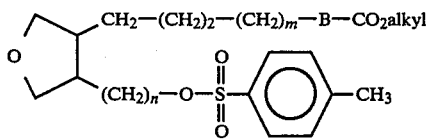

Thereafter, tosylate IX or IXA is reacted with a thiol of the structure

 R¹SH     X employing a molar ratio of IX or IXA:thiol of within the range of from about 0.8:1 to about 1:1, in a solvent such as tetrahydrofuran and in the presence of potassium t-butoxide to form the sulfide XI or XIA

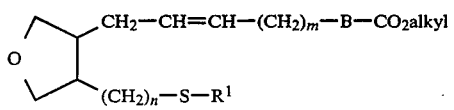

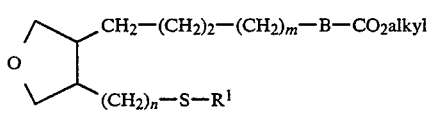

To form the sulfinyl and/or sulfonyl analogs (where n'=1), sulfide derivative XI or XIA is subjected to oxidation, for example, by reacting same with sodium periodate, in the presence of methanol and tetrahydrofuran, to form the sulfinyl derivative XII or XIIA and the sulfonyl derivative XIII or IIIA. The sulfinyl and sulfonyl derivatives may be separated by chromatography or other conventional separation procedures.

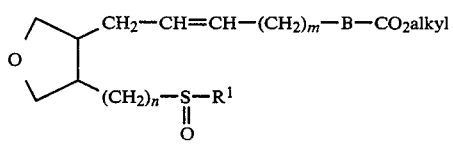

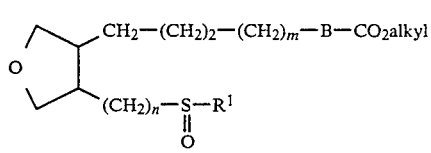

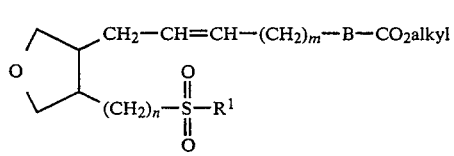

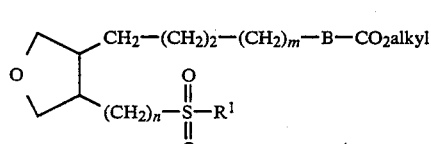

Compounds of Formula I wherein n is 2 to 4, may be prepared starting with the starting lower alkyl ester containing the hydroxymethyl group, that is, compound III or VI which is used to form the aldehyde II' (where A is —CH═CH—) or II" (where A is —(CH₂)₂).

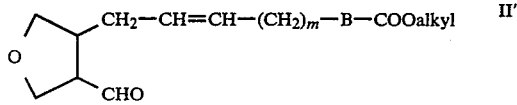

(includes cis and/or trans)

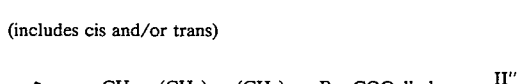

Thus, to form aldehyde II' where A is —CH═CH—, compound III or VI is subjected to a Collins oxidation, for example, by reacting III or VI with chromium trioxide in pyridine. To form the aldehyde II" (where A is (CH₂)₂), compound III or VI is reduced, for example, with hydrogen over a palladium on carbon catalyst, to form hydroxymethyl compound IIIA or VIA as described above and compound IIIA or VIA is subjected to a Collins oxidation to form aldehyde II" (where A is (CH₂)₂ including all isomers).

The aldehyde II' or II" is used to prepare aldehyde XV (where n is 2-4) by carrying out a homologation sequence, such as a witting reaction with (C₆H₅)₃P═CHOMe followed by hydrolysis (n-1) times, as shown below.

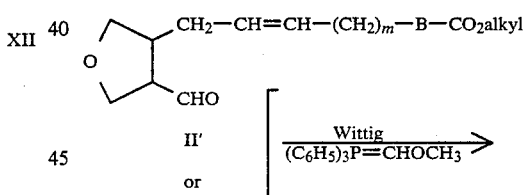

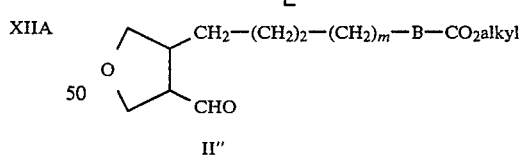

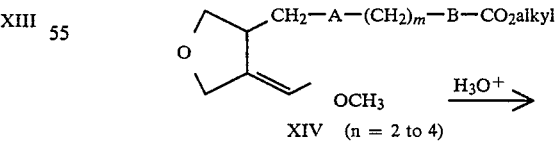

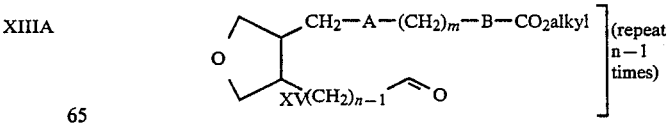

The aldehyde XV (where n is 2–4) is thus carried on to compounds of this invention where n is 2–4, that is

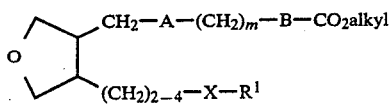  IA or IB (IA where A is —CH═CH—)
(IB where A is (CH₂)₂)
by reducing aldehyde XV employing a reducing agent such as sodium borohydride or sodium cyanoborohydride in a solvent such as methanol to form the alcohol ester XVI

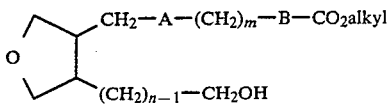  XVI which is subjected to a tosylation/mesylation reaction as described above to form the corresponding tosylate/mesylate which in turn is subjected to ether formation by reaction with

Y—R¹     IV or

R¹SH     A as described above to form either IC or thioether ID

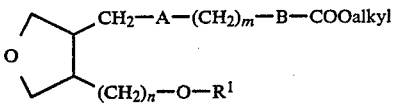  IC

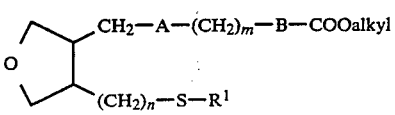  ID

The sulfinyl derivatives (where n is 2 to 4) and sulfonyl derivatives (where n is 2 to 4) are prepared by subjecting thioether ID (n'=0) to an oxidation reaction as described above to form a mixture of sulfinyl (n'=1) and sulfonyl derivatives (n'=2).

The above sulfinyl and sulfonyl derivatives may be separated by chromatography or other conventional separation procedures.

The various esters XI, XIA, XII, XIIA, XIII, XIIIA, IA, IB, IC, and ID can be converted to the free acid, that is, to

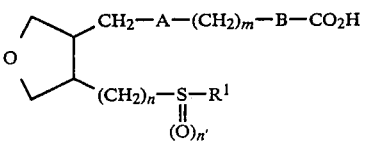  IE by treatment of the esters with an alkali metal hydroxide, such as lithium or sodium hydroxide to form the alkali metal salt, followed by neutralization with an acid, such as dilute hydrochloric acid or oxalic acid to form the acid IE.

Compounds of the invention wherein B is —CH═CH— and A is CH═CH or (CH₂)₂ may be prepared as follows. The tetrahydrofuranyl ether or thio ether of the structure XVII

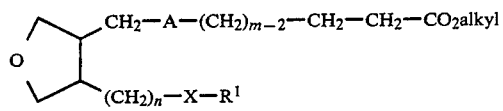  XVII is subjected to phenylselenylation by reacting XVII with lithium temperatures of from about 0° to about −78° C. in the presence of an inert organic solvent such as tetrahydrofuran, dimethoxy ethane or ether; thereafter a solution of diphenyldiselenide in an inert organic solvent as described above is added and the reaction is maintained at reduced temperatures as described above to form the selenophenyl ester XVIII

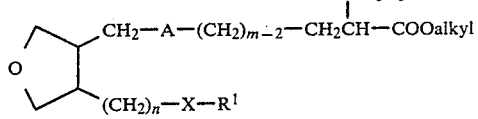  XVIII

The selenophenyl ester XVIII is next hydrolyzed by reaction with a strong base such as LiOH, K₂CO₃ or NaOH and then treated with strong acid such as HCl as described hereinbefore to form acid XIX

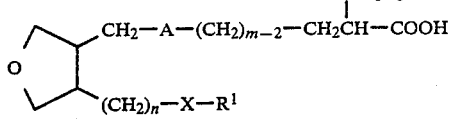  XIX

The selenophenyl acid XIX is then made to undergo a selenoxide elimination reaction wherein the selenophenyl acid is treated with hydrogen peroxide in an inert organic solvent such as tetrahydrofuran to form acid XX

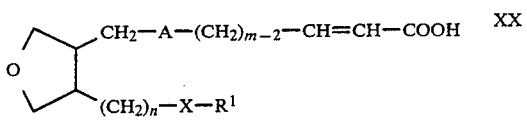  XX

The tris(hydroxymethyl)aminomethane salt of any of the acids of formula I of the present invention is formed by reacting a solution of such acid in an inert solvent such as methanol with tris(hydroxymethyl)aminomethane and thereafter the solvent is removed by evaporation to leave the desired salt.

The aldehyde intermediate II

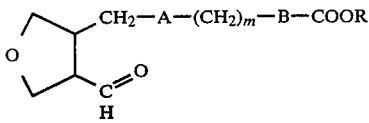  II wherein A is —CH═CH may be prepared as follows.
1-Trimethylsilyloxy-1,3-butadiene A in an inert organic solvent such as methylene chloride, ether or tetrahydrofuran is made to react with maleic anhydride B in a Diels-Alder reaction to form the anhydride C

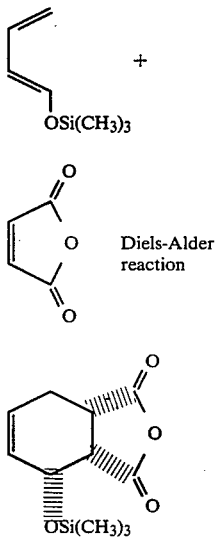

A

B

Diels-Alder reaction

C

The anhydride C is reduced, for example, by treatment with a reducing agent such as lithium aluminum hydride, in the presence of an inert organic solvent such as tetrahydrofuran to form triol D

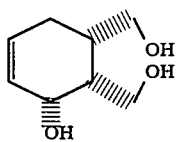

D

The triol D is then made to undergo acetonide formation by reacting D with p-toluene sulfonic acid in an inert organic solvent such as acetone, or with 2,2-dimethoxy propane or 2-methoxypropene in methylene chloride and under an inert atmosphere to form acetonide E

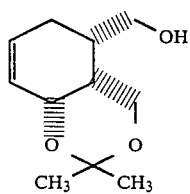

E

Acetonide E is then tosylated by reacting D in a solution of methylene chloride and weak organic base such as pyridine, with p-toluenesulfonyl chloride to form the tosylate F

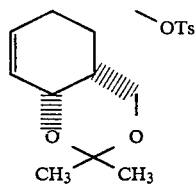

F

Tosylate F is then hydrolyzed by treatment with strong acid, such as HCl, oxalic acid or amberlyst resin/methanol in the presence of an inert organic solvent such as tetrahydrofuran to form alcohol G

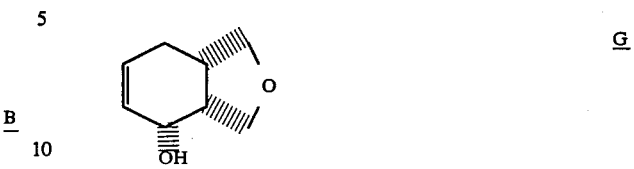

G

Next, the alcohol G is benzylated by reacting G with benzylbromide in the presence of sodium hydride and an inert organic solvent such as dimethylformamide to form benzylether H

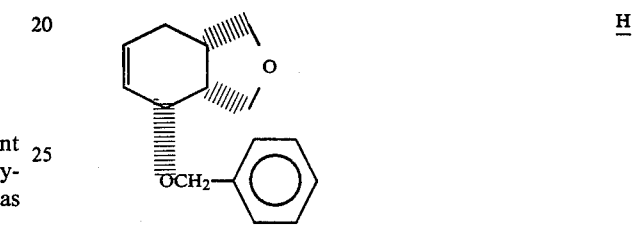

H which is then made to undergo osmylation by reacting H with osmium tetroxide in the presence of N-methylmorpholine-N-oxide and appropriate inert organic solvent such as tetrahydrofuran to form diol J

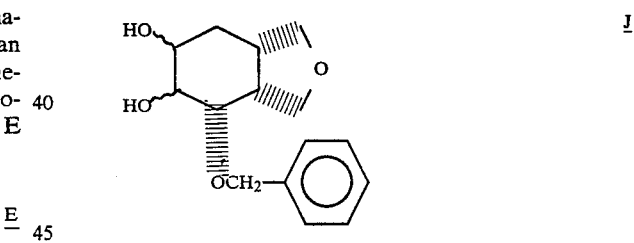

J

The diol J is next subjected to periodate cleavage by reacting diol J in an alcohol solvent such as methanol with sodium metaperiodate to form dialdehyde K

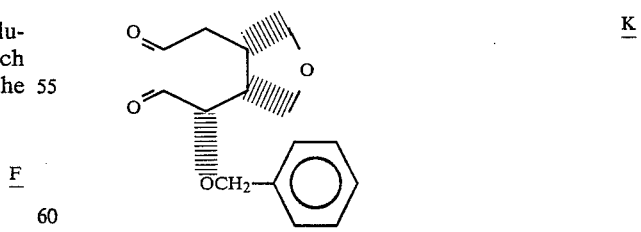

K

The dialdehyde K is then reduced by treatment with lithium aluminum hydride or other reducing agent such as sodium borohydride or lithium borohydride in the presence of an inert organic solvent such as methanol or tetrahydrofuran, to form the diol L

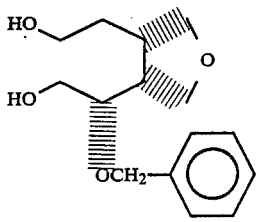

L which is then made to undergo hydrogenolysis by treatment of L with hydrogen in the presence of a palladium over carbon catalyst in ethyl acetate and glacial acetic acid, to form triol M

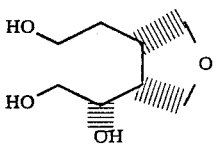

M

The triol M is next subjected to acetonide formation by reacting M with p-toluenesulfonic acid in the presence of an inert organic solvent such as acetone, to form the alcohol N

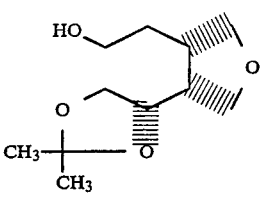

N which is oxidized by reacting with pyridinium chlorochromate in the presence of an inert organic solvent such as methylene choride or with chromium trioxide in pyridine, to form aldehyde O

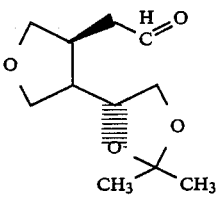

O

Aldehyde O is next subjected to a Wittig reaction wherein a mixture of triphenylphosphonium compound P

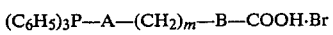

P such as (4-carboxybutyl)-triphenylphosphonium bromide salt in tetrahydrofuran and potassium t-amylate in toluene is reacted with aldehyde O to form acid Q

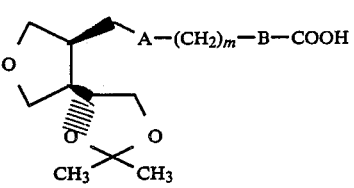

Q which is then dissolved in ether and reacted with a diazoalkane such as diazomethane to form ester R

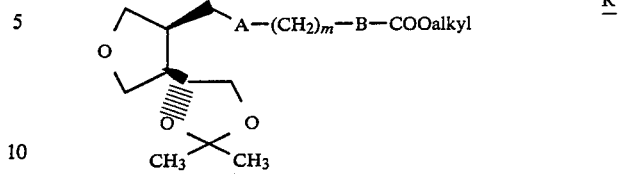

R

Ester R is then made to undergo acetal exchange by reacting R in methanol with p-toluene sulfonic acid to form diol S

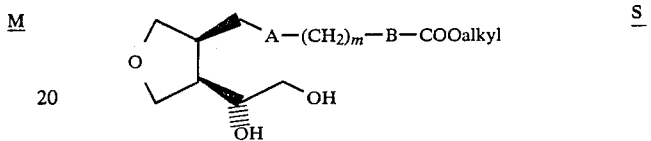

S which is then subjected to periodate cleavage by reacting S in methanol with sodium metaperiodate to form aldehyde IIA

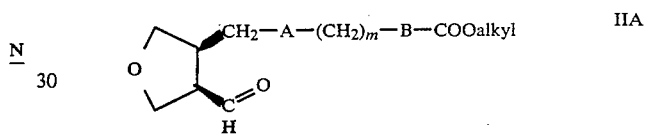

IIA (wherein A is CH=CH)

The intermediate aldehyde of formula II wherein A is —(CH$_2$)$_2$— are prepared by reducing compound S by treatment with hydrogen in the presence of palladium on charcoal to form compound S'

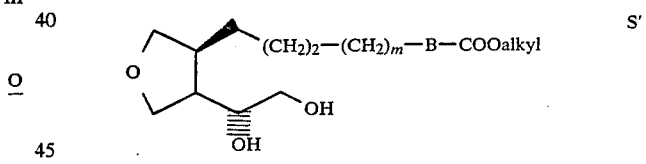

S' which is subjected to periodate cleavage as described above form aldehyde IIAA

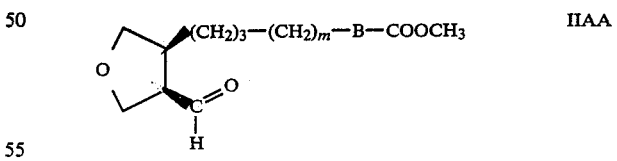

IIAA which may then be hydrolyzed to the corresponding acid XIX by treatment with alkali metal hydroxide and then HCl as described hereinbefore.

The compounds of this invention have three centers of asymmetry as indicated by the asterisks in formula I. However, it will be apparent that each of the formulae set out above which do not include asterisks still represent all of the possible stereoisomers thereof. All of the various stereoisomeric forms are within the scope of the invention.

The various stereoisomeric forms of the compounds of the invention, namely, cis and trans forms and stereoisomeric pairs may be prepared as shown in the working Examples which follow. Examples of such stereoisomers are set out below.

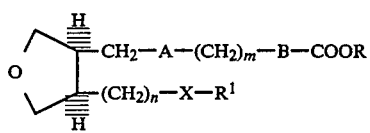

(cis)

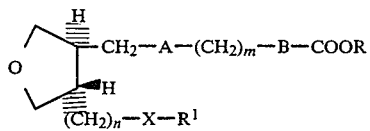

(trans)

The compounds of this invention are cardiovascular agents useful as platelet aggregation inhibitors, such as inhibiting arachidonic acid-induced platelet aggregation (e.g., for treatment of thrombolytic disease, such as coronary or cerebral thromboses) and in inhibiting bronchoconstriction as induced by asthma. They are also selective thromboxane $A_2$ receptor antagonists and synthetase inhibitors, e.g., having a vasodilatory effect for treatment of myocardial ischemic disease, such as angina pectoris. The compounds of the invention are also arachidonic acid cyclo-oxygenase inhibitors. In addition, the compounds of the invention are useful as analgesic agents in the manner of aspirin and indomethacin in the manner of aspirin and indomethacin as indicated by reaction thresholds to pressure in edematous hindpaws [Ref: Winter et al, J. Pharmacol, Exp. Ther. 150:165, 1965] and as antiinflammatory agents in mammals, as indicated by carrageenin-induced edema in the rat [Ref: Winter et al., J. Pharmacol., Exp. Ther. 141:369, 1963]. They may be used to decrease joint swelling, tenderness, pain and stiffness in conditions such as rheumatoid arthritis.

The compounds of the invention can be administered orally or parenterally to various mammalian species known to be subject to such maladies, e.g., cats, dogs, and the like in an effective amount within the dosage range of about 1 to 100 mg/kg, preferably about 1 to 50 mg/kg and especially about 2 to 25 mg/kg on a regimen in single or 2 to 4 divided daily doses.

The compounds of the invention may also be administered topically to any of the above mammalian species in amounts of from about 0.1 to 10 mg/kg in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain members additionally serve as intermediates for other members of the group.

The compounds of this invention may also be administered topically to treat peripheral vascular diseases and as such may be formulated as a cream or ointment.

The following Examples represent preferred embodiments of the invention. Unless otherwise indicated, all temperatures are expressed in degrees Centigrade.

EXAMPLE 1

[3α(Z),4α]-7-[4-[(Hexyloxy)methyl]tetrahydro-3-furanyl]-5-heptenoic acid

A.

[3α(Z),4α]-7-[Tetrahydro-4-formyl-3-furanyl]-5-heptenoic acid, methyl ester (1) (1α,2β,3β)-1-Trimethylsilyloxy-cyclohex-5-ene, 2,3-dicarboxylic acid anhydride To a solution of 28.4 g of 1-trimethylsilyloxy-1,3-butadiene (0.2 mole) in 200 ml of $CH_2Cl_2$ at 25° C. was added 19.6 g of maleic anhydride (0.2 mole). The mixture was stirred at 25° C. for 24 hours then concentrated. The residue was purified on a LPS-1 silica gel column, eluting with 5% EtOAc/hexanes (3 liters) and 20% EtOAc/hexanes (4 liters) to give 26.0 g of title anhydride as a light yellow oil.

(2) (1α,2β,3β)-1-Hydroxy-cyclohex-5-ene, 2,3-dimethanol

To a suspension of 8.0 g of lithium aluminum hydride (210.5 mmole, 2 eq.) in 200 ml of dry THF at 0° C. was added slowly, a solution of 25 g of title A (1) anhydride (104 mmole) in 150 ml of dry THF. The reaction was stirred at reflux for 4 hours and at 25° C. for 18 hours, then cooled to 0° C. and a saturated solution of $Na_2SO_4$ was added dropwise until no more white precipitates formed. It was then filtered. The white precipitates were washed thoroughly with THF, then stirred with 500 ml of 10% acetonitrile in ethylacetate for 30 minutes and filtered. The combined filtrate was concentrated to give a viscous oil which was purified on a LPS-1 silica gel column, eluting with 50% EtOAc/hexanes and 5% methanol/EtOAc to give 14.98 g of title triol as a clear oil.

(3)(1α,9β,10β)-1-Hydroxymethyl-6,6-dimethyl-3,4-dehydro-5,7-dioxa-octalin

To a solution of 14.98 g of title A (2) triol (95 mmole) in 150 ml of dry acetone was added 30 g of dried 4A molecular sieves and 1 g of p-toluenesulfonic acid (5 mmole, 5 mole %). After stirring at 25° C. under an argon atmosphere for 18 hours, the reaction mixture was neutralized with solid sodium bicarbonate and filtered. The filtrate was concentrated to give an oil which was purified on a LPS-1 silica gel column, eluting with 5% EtOAc/hexanes and 10% EtOAc//hexanes to give 15.58 g of the title acetonide.

(4)(1α,9β,10β)-1-Toluenesulfonyloxymethyl-6,6-dimethyl-3,4-dehydro-5,7-dioxa-octalin To a solution of 6 g of title A (3) acetonide (30 mmole) in 40 ml of dry methylene chloride and 20 ml of pyridine (150 mmole, 5 eq.) was added 7.63 g of p-toluenesulfonylchloride (40 mmole, 1.3 eq.). After stirring at 25° C. for 24 hours, the reaction mixture was diluted with ether and washed with water, 1N hydrochloric acid and brine. The aqueous layer was back-extracted with ether. The combined organic layer was dried over anhydrous $MgSO_4$ and concentrated to give title tosylate in the form of an oil which was used directly in the next reaction.

(5)
(4α,8β,9β)-4-Hydroxy-1,3,4,7,8,9-hexahydro-isobenzofuran

To a solution of crude title A (4) tosylate (6.30 mmole) in 40 ml of dry THF and 10 ml of H$_2$O was added 20 ml of a 1N aqueous HCl solution. After stirring for 6 hours at 25° C., the reaction was neutralized with solid NaHCO$_3$ and diluted with methylene chloride. The layers were separated. The aqueous layer was extracted with methylene chloride. The combined organic layer was dried over anhydrous MgSO$_4$ and concentrated to give an oil which was purified on an LPS-1 silica gel column, eluting with 5–10% EtOAc/hexanes to give 3.85 g of title alcohol.

(6)
(4α,8β,9β)-4-Benzyloxy-1,3,4,7,8,9-hexahydro-isobenzofuran

To a slurry of 1.44 g of prewashed sodium hydride (50% dispersion in mineral oil, 27.0 mmole, 1.6 eq.) in 20 ml of dry DMF at 0° C. was added a solution of 3.85 g title A (5) alcohol (27.0 mmole) in 10 ml DMF. The mixture was stirred at 25° C. for 15 minutes, cooled to 0° C. and then 4.3 g of benzylbromide (27.0 mmole, 1.0 eq.) was added. After stirring for 30 minutes at 25° C., the reaction mixture was poured into 300 ml of a saturated aqueous ammonium chloride solution and extracted with three 100 ml of water, dried over anhydrous MgSO$_4$ and concentrated. The residue was purified on an LPS-1 silica gel column, eluting with 10% EtOAc/hexanes to give 4.5 g of title benzylether as a yellow oil.

(7)
(4α,8β,9β)-4-Benzyloxy-5,6-dihydroxyoctahydro-isobenzofuran

To 1.6 g of title A (6) benzylether (6.95 mmole) in 70 ml of dry THF at 25° C. was added 1.17 g of N-methylmorpholine-N-oxide (8.34 mmole, 1.2 eq.) followed by dropwise addition of water until a homogeneous solution was obtained. To the resulting solution at 25° C. was added 353 μmole of a 5% solution of osmium tetroxide in ether (67.5 μmole, 1%). After stirring at 25° C. for 2 hours, 30 ml of a saturated aqueous sodium bisulfite solution was added to the mixture which was stirred at 25° C. for 30 minutes and extracted with three 100 ml portions of CH$_2$Cl$_2$. The combined organic layer was washed with 50 ml of 1N HCl solution, 50 ml of H$_2$O, dried over anhydrous MgSO$_4$ and concentrated to give 1.6 g title diol as a light brown solid. This was used without purification.

(8)
[3α,4α(1S)]-2-[Tetrahydro-4-(1-benzyloxy-1-formylmethyl)-3-furanyl]acetaldehyde To 1.6 g title A (7) diol (6.06 mmole) in 40 ml of methanol at 25° C. was added a solution of 1.48 g of sodium metaperiodate (6.0 mmole, 1.1 eq.) in 15 ml of water. After stirring at 25° C. for 1 hour, the reaction mixture was extracted with three 50 ml portions of CH$_2$Cl$_2$. The organic layer was dried over anhydrous MgSO$_4$ and concentrated to give 1.7 g title dialdehyde as a yellow oil. This was used without purification.

(9)
[3α,4α(1S)]-2-[Tetrahydro-4-(1-benzyloxy-1-hydroxymethylmethyl)-3-furanyl]ethanol To a slurry of 460 mg of lithium aluminum anhydride (12.1 mmole, 4 eq.) in 50 ml of dry THF at 0° C. was added slowly a solution of 1.7 g crude title A (8) dialdehyde (ca. 6.0 mmole) in 10 ml of dry THF. After stirring at 0° C. for 20 minutes, a saturated aqueous sodium sulfate solution was added dropwise until no more precipitates formed. The mixture was diluted with 300 ml of CH$_2$Cl$_2$ and stirred with anhydrous MgSO$_4$ for 30 minutes then filtered. The filtrate was concentrated to give 1.6 g title A(9) diol as a clear oil.

(10)
[3α,4α(1S)]-2-[Tetrahydro-4-(1-hydroxy-1-hydroxymethylmethyl)-3-furanyl]ethanol A mixture of 1.6 title A (9) diol, 1.6 g of 10% palladium over carbon in 80 ml of EtOAc and 4 ml of glacial acetic acid was shaken in a Parr bottle under 50 lb. of hydrogen pressure at 25° C. for 24 hours. The mixture was then filtered through a bed of Celite. The filtrate was concentrated to give title A (10) triol as a clear oil. This oil was used without purification.

(11)
(3α,4α)-2-[Tetrahydro-4-(4,4-dimethyl-3,5-dioxacyclopentyl)-3-furanyl]ethanol To title A (10) triol (ca. 6.0 mmole) in 20 ml of dry acetone was added 113 mg of p-toluene-sulfonic acid (0.6 mmole, 10%) and 1.0 g of molecular sieves type 4 Å. After stirring at 25° C. for 4 hours, the reaction mixture was neutralized by addition of 80 mg solid sodium bicarbonate and filtered. The filtrate was concentrated to give a crude oil which was purified on a silica gel column, eluting with 50% EtOAc/hexanes (2 liters) and 3% MeOH/CH$_2$Cl$_2$ (1 liter) to give 1.0 g of title A (11) alcohol as a clear oil.

(12)
(3α,4α)-2-[Tetrahydro-4-(4,4-dimethyl-3,5-dioxacyclopentyl)-3-furanyl]acetaldehyde To 300 mg of title A (11) alcohol (1.4 mmole) in 10 ml of CH$_2$Cl$_2$ was added 1.0 g of Celite, followed by 595 mg of pyridinium chlorochromate (2.8 mmole, 2 eq.). After stirring for 2 hours at 25° C., the reaction mixture was diluted with 100 ml of ether and filtered through a bed of florosil. The filtrate was concentrated to give title A (12) aldehyde as a clear oil. This was used directly in the next reaction.

(13)
[3α(Z),4α]-7-[Tetrahydro-4-(4,4-dimethyl-3,5-dioxacyclopentyl)-3-furanyl]-5-heptenoic acid and

(14)
[3α(Z),4α]-7-[Tetrahydro-4-(4,4-dimethyl-3,5-dioxacyclopentyl)-3-furanyl]-5-heptenoic acid To 927 mg of (4-carboxybutyl)-triphenylphosphonium bromide salt (2.1 mmole, 1.5 eq.) in 5 ml of dry THF at 0° C. was added dropwise 2.7 ml of a 1.43M solution of potassium t-amylate in toluene (3.9 mmole, 2.8 eq.). The mixture was stirred at 25° C. for 2 hours, cooled to 0° C. and a solution of title A (12) aldehyde in 15 ml of THF (ca. 1.4 mmole) was added dropwise. After stirring at 25° C. for 1 hour, the reaction was quenched with glacial acetic acid and poured into 300 ml of brine and extracted with three 50 ml portions of EtOAc. The combined organic layer was concentrated. The residue was diluted with 50 ml of a saturated sodium bicarbonate solution, then extracted with three 50 ml portions of EtOAc. The aqueous layer was acidified to pH 5 with glacial acetic acid and extracted with four 50 ml portions of $CH_2Cl_2$. The organic layer was dried over anhydrous $MgSO_4$ and concentrated to give title A (13) acid as a oil. This oil was dissolved in ether and methanol and treated with excess $CH_2N_2$ in ether to give 400 mg of a yellow oil after concentration. Purification was done on a silica gel column, eluting with 30% EtOAc/hexanes to give 210 mg of title A (14) ester as a yellow oil.

(15)
[3α(Z),4α(1S)]-7-[Tetrahydro-4-[(1-hydroxy-1-hydroxymethyl)methyl]-3-furanyl]-5-heptenoic acid, methyl ester To 180 mg of title A (14) ester (0.57 mmole in 2 ml of methanol was added 5.4 mg of p-toluene sulfonic acid (28.8 μm, 5%). The mixture was stirred at 25° C. for 4 hours, then concentrated. The residue was dissolved in 2 ml of fresh methanol and stirred at 25° C. for 18 hours, then concentrated. The residue was diluted with 30 ml of ether and filtered through a bed of silica gel. The filtrate was concentrated to give 127 mg of title diol as a clear oil.

(16)
[3α(Z),4α]-7-[Tetrahydro-4-formyl-3-furanyl]-5-heptenoic acid, methyl ester To a solution of 127 mg of title A (15) diol (0.40 mmole) in 5 ml of methanol at 25° C. was added a solution of 107 mg of sodium metaperiodate in 1 ml of $H_2O$. The mixture was stirred at 25° C. for 30 minutes, then extracted with three 10 ml portions of $CH_2Cl_2$. The organic layer was dried over anhydrous $MgSO_4$ and concentrated to give title aldehyde as a clear oil.

B.
[3α(Z),4α]-7-[(4-Hydroxymethyl)tetrahydro-3-furanyl]-5-heptenoic acid, methylester To 136.8 mg of title A aldehyde (0.57 mmole) in 2 ml of methanol at 0° C. was added 21.7 mg of sodium borohydride (0.57 mmole, 4 eq.). After stirring for 15 minutes, the mixture was poured into 100 ml of a saturated ammonium chloride solution and extracted with three 30 ml portions of ether. The organic layer was dried over anhydrous $MgSO_4$ and concentrated to give 128 mg of title alcohol. This was used without purification.

C.
[3α(Z),4α]-7-[4-[(Hexyloxy)methyl]tetrahydro-3-furanyl]-5-heptenoic acid

A solution of 280 mg of potassium hydroxide (5 mmole, 10 eq.) in 20 ml of dry xylene was distilled off until about 10 ml of the solution remained. To this solution was added a solution of 120 mg of title B alcohol (0.5 mmole) in 20 ml of dry xylene. The mixture was heated to reflux and 10 ml of xylene was again distilled off. To the cooled remaining solution was added a solution of 430 mg of hexylmesylate (2.5 mmole, 5 eq.) in 10 ml of dry xylene. The resulting mixture was refluxed for 3 hours, cooled to 25° C., diluted with 100 ml of $H_2O$, and extracted with three 50 ml portions of ether. The combined ethereal extract was washed with two 30 ml portions of $H_2O$, dried over anhydrous $MgSO_4$ and concentrated.

The residue was purified on a CC-7 silica gel column, eluting with a gradient of pentane/ether. The product thus collected was kept under high vacuum for 2 days to yield 37 mg of title compound as a clear oil.

TLC: Silica gel; 7% $MeOH/CH_2Cl_2$; $R_f \sim 0.45$.

Anal Calcd for $C_{18}H_{32}O_4$ 0.13 $H_2O$: C, 68.69; H, 10.33 Found: C, 68.69; H, 10.36

EXAMPLE 2

[3α(Z),4β]-7-[4-(Hexyloxy)methyl]tetrahydro-3-furanyl]-5-heptenoic acid, hexyl ester A.
[3α(Z),4β]-7-[Tetrahydro-4-formyl-3-furanyl]-5-heptenoic acid, methyl ester To 140 mg of [3α(Z),4α]-7-[tetrahydro-4-formyl-3-furanyl]-5-heptenoic acid, methyl ester (prepared as described in Example 1, Part A (16) (0.58 mmole) in 2 ml of methanol was added 3.15 mg of sodium methoxide (58 μmole, 10%). After stirring at 25° C. for 2 hours, the reaction mixture was poured into 50 ml of a saturated aqueous ammonium chloride solution and extracted with three 10 ml portions of ether. The organic layer was washed with 10 ml of $H_2O$ and dried over anhydrous $MgSO_4$ and concentrated to give 130 mg of title aldehyde as an oil. This was used without purification.

B.
[3α(Z),4β]-7-[Tetrahydro-4-hydroxymethyl-3-furanyl]-5-heptenoic acid, methyl ester To 43 mg of title A aldehyde (0.18 mmole) in 1 ml of methanol at 0° C. was added 6.8 mg of sodium borohydride (0.18 mmole, 4 eq.). After stirring at 0° C. for 10 minutes, the mixture was poured into 20 ml of a saturated $NH_4Cl$ solution and extracted with three 10 ml portions of ether. The combined ethereal extract was dried over anhydrous $MgSO_4$ and concentrated to give 44 mg of title alcohol as an oil.

C.
[3α(Z),4β]-7-[4-[(Hexyloxy)methyl]tetrahydro-3-furanyl]-5-heptenoic acid, hexyl ester To 100 mg of powdered potassium hydroxide (1.8 mmole, 10 eq.) in 20 ml of dry xylene was added a solution of 44 mg of title B alcohol (0.18 mmole) in 20 ml of dry xylene. The mixture was heated to reflux and ca. 20 ml of xylene was distilled off.

To the cooled remaining solution was added a solution of 309 mg of hexyl mesylate (1.8 mmole, 10 eq.) and the mixture was heated at reflux for 3 hours. The mixture was cooled to 25° C., diluted with 100 ml of ether and washed with two 20 ml portions of water. The organic layer was dried over anhydrous $MgSO_4$ and concentrated to give an oil which was purified on a silica gel column, eluting with 10% EtOAc/hexanes to yield 45 mg of title ester as a yellow oil.

EXAMPLE 3

[3α(Z),4β]-7-[4-[(Hexyloxy)methyl]tetrahydro-3-furanyl]-5-heptenoic acid

To 45 mg of Example 2 title C ester (0.14 mmole) in 6 ml of THF was added 1.6 ml of 1M lithium hydroxide solution. The mixture was stirred at 25° C. for 4 days and then concentrated. The residue was diluted with 10 ml of $H_2O$ and acidified with a saturated oxalic acid solution to pH 3 and extracted with three 10 ml portions of ether. The combined ethereal extract was washed with two 10 ml portions of water, dried over anhydrous MgSO$_4$ and concentrated.

The residue was purified on a CC-7 silica gel column, eluting with a gradient of pentane/ether. The product was kept under high vacuum for 2 days to yield 28 mg of title compound as an oil. TLC: silica gel; 5% MeOH/CH$_2$Cl$_2$; R$_f$~0.4.

Anal Calcd for C$_{18}$H$_{32}$O$_4$: C, 69.14; H, 10.32 Found: C, 68.94; H, 10.39

EXAMPLE 4

[3α(Z),4α]-7-[4-[(Hexylthio)methyl]tetrahydro-3-furanyl]-5-heptenoic acid, methyl ester

A.

[3α(Z),4α]-7-[(4-p-toluenesulfonyloxymethyl)tetrahydro-3-furanyl]-5-heptenoic acid, methyl ester To 75 mg of [3α(Z),4α]-7-[tetrahydro-4-hydroxymethyl-3-furanyl]-5-heptenoic acid, methyl ester (prepared as described in Example 1 Part B (0.35 mmole) in 1 ml of pyridine at 25° C. was added 90 mg of p-toluenesulfonyl chloride (0.39 mmole, 1.1 equiv.). The mixture was stirred at 25° C. for 1.5 hours, then diluted with 30 ml of ether. The ethereal solution was washed with two 10 ml portions of a saturated cupric sulfate solution, 20 ml of H$_2$O, then dried over anhydrous MgSO$_4$ and concentrated. Purification was done on a silica gel column, eluting with 25% EtOAc/hexane to yield 70 mg of title compound as an oil.

B.

[3α(Z),4α]-7-[4-[(Hexylthio)methyl]tetrahydro-3-furanyl]-5-heptenoic acid

To 50 ml of hexanethiol (0.35 mmol, 2 equiv.) in 1 ml of dry THF was added 24.7 mg of potassium t-butoxide (0.22 mmole, 1.3 equiv.). After stirring at 25° C. for 30 minutes, a solution of 70 mg of title A tosylate in 1 ml of THF was added and the mixture was heated at reflux for 1 hour. The cooled mixture was diluted with 30 ml of ether and washed with two 10 ml portions of saturated NaHCO$_3$ and two 10 ml portions of H$_2$O. The organic layer was dried over anhydrous MgSO$_4$ and concentrated.

The residue was purified on a silica gel column, eluting with 30% EtOAc/hexane to give 37 mg of title ester as an oil.

EXAMPLE 5

[3α(Z),4α]-7[4-[(Hexylthio)methyl]tetrahydro-3-furanyl]-5-heptenoic acid

To a solution of 37 mg of Example 4 title B ester in 4 ml of THF, saturated with argon, was added at 25° C. 1 ml of a 1M lithium hydroxide solution. The mixture was stirred at 25° C. under an argon atmosphere for 20 hours and then concentrated. The residue was diluted with 5 ml of H$_2$O, acidified to pH 3 with a saturated oxalic acid solution, extracted with three 20 ml portions of ether. The ethereal solution was washed with two 15 ml portions of H$_2$O, dried over anhydrous MgSO$_4$ and concentrated.

The product was kept under high vacuum for 2 days to yield 30 mg of title acid as an oil.
TLC: silica gel; 5% MeOH/CH$_2$Cl$_2$; R$_f$~0.35
Anal Calcd for C$_{18}$H$_{32}$O$_3$S: C, 65.81; H, 9.76 Found: C, 65.57; H, 9.82

EXAMPLE 6

[3α(Z),4α]-7-[4-[(Phenyloxy)methyl]tetrahydro-3-furanyl]-5-heptenoic acid (a) Phenol (1 mmole) is added to a solution of 262 mg triphenylphosphine (1 mmole), diethylazodicarboxylate (1 mmole) and Example 1, Part B (1 mmole) alcohol in 25 ml of dry THF and is stirred at 23° C. for 48 hours. The reaction mixture is concentrated in vacuo and the residue is triturated with ether. Filtration, concentration of the filtrate under reduced pressure and finally chromatgraphy of the residue on a silica gel column gives [3α(Z),4α]-7-[4-[(phenyloxy)methyl]tetrahydro-3-furanyl]-5-heptenoic acid, methyl ester.

(b) Following the procedure set out in Example 3, the ester from part (a) is converted to the title acid.

EXAMPLE 7

[3α(Z),4α]-7-[4-[(Benzyloxy)methyl]tetrahydro-3-furanyl]-5-heptenoic acid

Following the procedure of Example 1 except substituting benzyl mesylate for hexyl mesylate, the title compound is obtained.

EXAMPLE 8

[3α(Z),4α]-7-[4-[(Cyclohexyloxy)methyl]tetrahydro-3-furanyl]-5-heptenoic acid

Following the procedure of Example 1 except substituting cyclohexyl mesylate for hexyl mesylate, the title compound is obtained.

EXAMPLE 9

[3α(Z),4α]-7-[4-[(2-Pentenyloxy)methyl]tetrahydro-3-furanyl]-5-heptenoic acid

Following the procedure of Example 1 except substituting 2-pentenyl-1-mesylate for hexyl mesylate, the title compound is obtained.

EXAMPLE 10

[3α(Z),4α]-7-[4-[(Cyclopentylmethyloxy)methyl]tetrahydro-3-furanyl]-5-heptenoic acid Following the procedure of Example 1 except substituting cyclopentylmethyl mesylate for hexyl mesylate, the title compound is obtained.

EXAMPLE 11

[3α(Z),4β]-7-[4-[(Heptyloxy)methyl]tetrahydro-3-furanyl]-5-heptenoic acid

Following the procedure of Examples 2 and 3 except substituting heptyl mesylate for hexyl mesylate, the title compound is obtained.

EXAMPLE 12

[3α(Z),4β]-7-[4-[(Phenethyloxy)methyl]tetrahydro-3-furanyl]-5-heptenoic acid

Following the procedure of Examples 2 and 3 except substituting phenethyl mesylate for hexyl mesylate, the title compound is obtained.

EXAMPLE 13

[3α(Z),4β]-7-[4-[(Cyclopentyloxy)methyl]tetrahydro-3-furanyl]-5-heptenoic acid

Following the procedure of Examples 2 and 3 except substituting cyclopentyl mesylate for hexyl mesylate, the title compound is obtained.

EXAMPLE 14

[3α(Z),4β]-7-[4-[(Cyclohexyloxy)methyl]tetrahydro-3-furanyl]-5-heptenoic acid

Following the procedure of Examples 2 and 3 except substituting cyclohexyl mesylate for hexyl mesylate, the title compound is obtained.

EXAMPLE 15

[3α(Z),4β-7-[4-[(3-Butenyloxy)methyl]tetrahydro-3-furanyl]-5-heptenoic acid

Following the procedure of Examples 2 and 3 except substituting 3-butenyl mesylate for hexyl mesylate, the title compound is obtained.

EXAMPLE 16

[3α(Z),4α]-7-[4-[(2-Hexenylthio)methyl]tetrahydro-3-furanyl]-5-heptenoic acid

Following the procedure of Examples 4 and 5 except substituting 2-hexenyl-1-thiol for hexanethiol, the title compound is obtained.

EXAMPLE 17

[3α(Z),4α-7-[4-[(Propylthio)methyl]tetrahydro-3-furanyl]-5-heptenoic acid

Following the procedure of Examples 4 and 5 except substituting propylthiol for hexanethiol, the title compound is obtained.

EXAMPLE 18

[3α(Z),4α]-7-[4-[(Cycloheptylthio)methyl]tetrahydro-3-furanyl]-5-heptenoic acid

Following the procedure of Examples 4 and 5 except substituting cycloheptylmercaptan for hexanethiol, the title compound is obtained.

EXAMPLE 19

[3α(Z),4α]-7-[4-[(Benzylthio)methyl]tetrahydro-3-furanyl]-5-heptenoic acid

Following the procedure of Examples 4 and 5 except substituting benzylmercaptan for hexanethiol, the title compound is obtained.

EXAMPLE 20

[3α(Z),4α]-7-[4-[(Phenylthio)methyl]tetrahydro-3-furanyl]-5-heptenoic acid

Following the procedure of Examples 4 and 5 except substituting phenylmercaptan for hexanethiol, the title compound is obtained.

EXAMPLE 21

(3α,4α)-7-[4-[(Hexyloxy)methyl]tetrahydro-3-furanyl]-heptanoic acid

A.

[3α,4α(1S)]-7-[Tetrahydro-4-[(1-hydroxymethyl)methyl]-3-furanyl]heptanoic acid, methyl ester A mixture of 600 mg of Example 1 Part A (15) diol, 100 mg of a 10% palladium over carbon in 80 ml of EtOAc and 4 ml of glacial acetic acid is shaken in a Parr bottle under 50 lb. of hydrogen pressure at 25° C. for 24 hours. The mixture is then filtered through a bed of Celite. The filtrate is concentrated to give title A diol.

B.

(3α,4α)-7-[Tetrahydro-(1-formyl)-3-furanyl]heptanoic acid, methyl ester

To a solution of 600 mg of title A diol (1.9 mmole) in 5 ml methanol at 25° C. is added a solution of 490 mg of Na m-periodate in 1 ml $H_2O$. The mixture is stirred at 25° C. for 30 minutes, then extracted with 3–10 ml portions of $CH_2Cl_2$. The organic layer is dried over anhydrous $MgSO_4$ and concentrated to give title aldehyde.

C.

[3α,4α]-7-[4-[(Hexyloxy)methyl]tetrahydro-3-furanyl]-heptanoic acid

Following the procedure of Example 1 Parts B and C except substituting the above Part B aldehyde for the Example 1 Part A (16) aldehyde, the title acid is obtained.

EXAMPLE 22

(3α,4α)-7-[4-[(Benzyloxy)methyl]tetrahydro-3-furanyl]-heptanoic acid

Following the procedure of Example 21 except substituting benzyl mesylate for hexyl mesylate, the title compound is obtained.

EXAMPLE 23

(3α,4α)-7-[4-[(Phenyloxy)methyl]tetrahydro-3-furanyl]heptanoic acid

A.

(3α,4α)-7-[4-(Hydroxymethyl)tetrahydro-3-furanyl]-heptanoic acid, methyl ester

Following the procedure of Example 1 Part B except substituting Example 21, Part B aldehyde for Example 1 Part A aldehyde, the title alcohol is obtained.

B.

(3α,4α)-7-[4-[(Phenyloxy)methyl]tetrahydro-3-furanyl]heptanoic acid

Following the procedure of Example 6 except substituting the above title A alcohol for Example 1 Part B alcohol, the title compound is obtained.

EXAMPLE 24

(3α,4α)-7-[4-[(Cyclohexyloxy)methyl]tetrahydro-3-furanyl]heptanoic acid

Following the procedure of Example 21 except substituting cyclohexyl mesylate for hexyl mesylate, the title compound is obtained.

EXAMPLE 25

(3α,4α)-7-[4-[(2-Butenyloxy)methyl]tetrahydro-3-furanyl]heptanoic acid

Following the procedure of Example 21 except substituting 2-butenyl-1-mesylate for hexyl mesylate, the title compound is obtained.

EXAMPLE 26

(3α,4α)-7-[4-[(Benzyloxy)methyl]tetrahydro-3-furanyl]heptanoic acid

Following the procedure of Example 21 except substituting the Example 2 Part A aldehyde for the Example 1 Part A (16) aldehyde and substituting benzyl mesylate for hexyl mesylate, the title compound is obtained.

EXAMPLE 27

(3α,4α)-7-[4-[(Phenyloxy)methyl]tetrahydro-3-furanyl]heptanoic acid

A. (3α,4α)-7-[4-Formyl-tetrahydro-3-furanyl]heptanoic acid, methyl ester

Following the procedure of Example 2 Part B except substituting Example 21 Part B aldehyde for Example 2 Part A aldehyde, the title aldehyde is obtained.

B.
(3α,4β)-7-[4-[(Phenyloxy)methyl]tetrahydro-3-furanyl]heptanoic acid

Following the procedure of Example 23 except substituting the above Part A aldehyde for Example 21 Part B aldehyde in Example 23 Part A, the title acid is obtained.

EXAMPLE 28

(3α,4β)-7-[4-[(Cyclopropyloxy)methyl]tetrahydro-3-furanyl]heptanoic acid

Following the procedure of Example 21 except substituting the Example 2 Part A aldehyde for the Example 1 Part A (16) aldehyde and substituting cyclopropyl mesylate for hexyl mesylate, the title compound is obtained.

EXAMPLE 29

(3α,4β)-7-[4-[(Cyclopentylethyloxy)methyl]tetrahydro-3-furanyl]heptanoic acid

Following the procedure of Example 21 except substituting the Example 2 Part A aldehyde for the Example 1 Part A (16) aldehyde and substituting cyclopentylethyl mesylate for hexyl mesylate, the title compound is obtained.

EXAMPLE 30

(3α,4β)-7-[4-[(3-Hexenyloxy)methyl]tetrahydro-3-furanyl]heptanoic acid

Following the procedure of Example 21 except substituting the Example 2 Part A aldehyde for the Example 1 Part A (16) aldehyde and substituting 3-hexenyl-1-mesylate for hexyl mesylate, the title compound is obtained.

EXAMPLE 31

(3α,4α)-7-[4-[(Octylthio)methyl]tetrahydro-3-furanyl]heptanoic acid

Following the procedure of Example 21 Parts A and B and Examples 4 and 5 except substituting the Example 21 Part B aldehyde in Examples 4 and 5 for the Example 1 Parts A (16) aldehyde and substituting octylthiol for hexanethiol, the title compound is obtained.

EXAMPLE 32

(3α,4α)-7-[4-[(Phenylthio)methyl]tetrahydro-3-furanyl]heptanoic acid

Following the procedure of Example 21 Parts A and B and Examples 4 and 5, substituting the Example 21 Part B aldehyde for the Example 1 Part A (16) aldehyde in Examples 4 and 5 and substituting phenylmercaptan for hexanethiol, the title compound is obtained.

EXAMPLE 33

(3α,4α)-7-[4-[(Benzylthio)methyl]tetrahydro-3-furanyl]heptanoic acid

Following the procedure of Example 21 Parts A and B and Examples 4 and 5, substituting the Example 21 Part B aldehyde for the Example 1 Part A (16) aldehyde in Examples 4 and 5 and substituting benzylmercaptan for hexanethiol, the title compound is obtained.

EXAMPLE 34

(3α,4α)-7-[4-[(Cyclopentylthio)methyl]tetrahydro-3-furanyl]heptanoic acid

Following the procedure of Example 21 Parts A and B and Examples 4 and 5, substituting the Example 21 Part B aldehyde for the Example 1 Part A (16) aldehyde in Examples 4 and 5 and substituting cyclopentylmercaptan for hexanethiol, the title compound is obtained.

EXAMPLE 35

(3α,4α)-7-[4-[(Cyclohexylmethylthio)methyl]tetrahydro-3-furanyl]heptanoic acid

Following the procedure of Example 21 Parts A and B and Examples 4 and 5, substituting the Example 21 Part B aldehyde for the Example 1 Part A (16) aldehyde in Examples 4 and 5 and substituting cyclohexylmethylmercaptan for hexanethiol, the title compound is obtained.

EXAMPLE 36

(3α,4α)-7-[4-[(2-Octenylthio)methyl]tetrahydro-3-furanyl]heptanoic acid

Following the procedure of Example 21 Parts A and B and Examples 4 and 5, substituting the Example 21 Part B aldehyde for the Example 1 Part A (16) aldehyde in Examples 4 and 5 and substituting 2-octenyl-1-thiol for hexanethiol, the title compound is obtained.

EXAMPLE 37

[3α(Z),4α]-7-[4-[2-(Hexyloxy)ethyl]tetrahydro-3-furanyl]-5-heptenoic acid

A.
[3α(Z),4α]-7-[4-[2-(2-Oxo)ethyl]tetrahydro-3-furanyl]-5-heptenoic acid, methyl ester Into a dry 100 ml round bottom 3-necked flask containing a stir bar is added dried 3.27 g (9.54 mmoles)

methoxymethyltriphenylphosphonium chloride ((C$_6$H$_5$)$_3$P$^+$-CH$_2$OCH$_3$Cl$^-$) and 30 ml distilled toluene (stored over molecular sieves). The resulting suspension is stirred in an ice-bath, under argon, until cold and then a 1.4M solution of 5.73 ml (8.01 mmol) of potassium t-amylate in toluene is added dropwise. A bright red solution formed which is stirred at 0° C. for an additional 35 minutes. Thereafter, a solution of 900 mg (3.75 mmol) [3α(Z),4α]-7-(4-formyl)tetrahydro-3-furanyl]-5-heptenoic acid, methyl ester (prepared as described in Example 1 Part A (16)) in 10 ml toluene is added by means of a dropping funnel over a 35 minute period with the ice-bath still in place. The reaction is then quenched by addition of 2.3 g (39 mmol) acetic acid in 5 ml ether. The reaction mixture is immediately poured into 200 ml saturated NH$_4$Cl, and extracted with ether (4×200 ml). The combined ether phases are washed with NaCl saturated solution, and dried (MgSO$_4$) and concentrated to yield an oil in a white crystalline solid (phosphine oxide). The white solid is triturated with EtOAc and the mother liquor is purified by chromatography on an LPS-1 silica column to obtain the enol-ether. The enol-ether is dissolved in 20 ml of THF and is then treated with 10 ml of a 20% aqueous trifluoroacetic acid solution. After 1 hour, trifluoroacetic acid is quenched by addition of solid NaHCO$_3$. The reaction mixture is extracted several times with methylene chloride. The methylene chloride extract is dried over anhydrous magnesium sulfate and concentrated under reduced pressure. The crude residue is chromatographed on a silica gel column to obtain the desired title A aldehyde.

B.

[3α(Z),4α]-7-[[4-(2-Hydroxyethyl)]tetrahydro-3-furanyl]-5-heptenoic acid, methyl ester The aldehyde (762 mg, 3 mmol) from part A in methanol (50 ml) is treated with NaBH$_4$ (0.11 g, 3 mmol) in an argon atmosphere at 0° C. After stirring at 0° C. for 1 hour, the reaction is quenched by addition of 2N HCl (to pH 2). The methanol is removed in vacuo and the reaction mixture is taken up in ether. The ether solution is washed with saturated KHCO$_3$, saturated NaCl and dried (MgSO$_4$). The ether is evaporated to yield the title B compound.

C.

[3α(Z),4α]-7-[[4-[2-(Hexyloxy)ethyl]tetrahydro-3-furanyl]-5-heptenoic acid

Following the procedure of Example 1, Part C and Example 2 except substituting the above part B alcohol for the Example 1 Part B alcohol used in Example 1 Part C, the title compound is obtained.

EXAMPLE 38

[3α(Z),4α]-7-[4-[2-(Hexylthio)ethyl]tetrahydro-3-furanyl]-5-heptenoic acid

Following the procedure of Examples 4 and 5 except substituting [3α(Z),4α]-7-[4-[2-(2-oxo)ethyl]tetrahydro-3-furanyl]-5-heptenoic acid, methyl ester (prepared as described in Example 37 Part A) for the Example 1 Part A (16) aldehyde used in Example 4, Part A, the title compound is obtained.

EXAMPLE 39

[3α(Z),4α]-7-[4-[2-(Benzyloxy)ethyl]tetrahydro-3-furanyl]-5-heptenoic acid

Following the procedure of Example 37 except substituting benzyl mesylate for hexyl mesylate, the title compound is obtained.

EXAMPLE 40

[3α(Z),4α]-7-[4-[2-(Phenyloxy)ethyl]tetrahydro-3-furanyl]-5-heptenoic acid

Following the procedure of Example 6 except substituting Example 37 Part B alcohol for Example 1 Part B alcohol, the title acid is obtained.

EXAMPLE 41

[3α(Z),4α]-7-[4-[2-(1-Butenyloxy)ethyl]tetrahydro-3-furanyl]-5-heptenoic acid

Following the procedure of Example 37 except substituting 1-butenyl mesylate for hexyl mesylate, the title compound is obtained.

EXAMPLE 42

[3α(Z),4α]-7-[4-[2-(Cyclohexyloxy)ethyl]tetrahydro-3-furanyl]-5-heptenoic acid

Following the procedure of Example 37 except substituting cyclohexyl mesylate for hexyl mesylate, the title compound is obtained.

EXAMPLE 43

[3α(Z),4α]-7-[4-[2-(Propyloxy)ethyl]tetrahydro-3-furanyl]-5-heptenoic acid

Following the procedure of Example 37 except substituting n-propyl mesylate for hexyl mesylate, the title compound is obtained.

EXAMPLE 44

[3α(Z),4α]-7-[4-[2-(Cyclopentylmethyloxy)ethyltetrahydro-3-furanyl-5-heptenoic acid Following the procedure of Example 37 except substituting cyclopentylmethyl mesylate for hexyl mesylate, the title compound is obtained.

EXAMPLE 45

[3α(Z),4α]-7-[4-[2-(Pentylthio)ethyl]tetrahydro-3-furanyl]-5-heptenoic acid

Following the procedure of Example 38 except substituting 1-pentanethiol for 1-hexanethiol, the title compound is obtained.

EXAMPLE 46

[3α(Z),4α]-7-[4-[2-(Benzylthio)ethyl]tetrahydro-3-furanyl]-5-heptenoic acid

Following the procedure of Example 38 except substituting benzylmercaptan for 1-hexanethiol, the title compound is obtained.

EXAMPLE 47

[3α(Z),4α]-7-[4-[2-(Phenylthio)ethyl]tetrahydro-3-furanyl]-5-heptenoic acid

Following the procedure of Example 38 except substituting phenylmercaptan for 1-hexanethiol, the title compound is obtained.

EXAMPLE 48

[3α(Z),4α]-7-[4-[2-(Cyclohexylthio)ethyl]tetrahydro-3-furanyl]-5-heptenoic acid

Following the procedure of Example 38 except substituting cyclohexylmercaptan for 1-hexanethiol, the title compound is obtained.

EXAMPLE 49

[3α(Z),4α]-7-[4-[2-(Cyclohexylmethylthio)ethyl]tetrahydro-3-furanyl]-5-heptenoic acid Following the procedure of Example 38 except substituting cyclohexylmethylmercaptan for 1-hexanethiol, the title compound is obtained.

EXAMPLE 50

[3α(Z),4α]-7-[4-[2-(1-Propenylthio)ethyl]tetrahydro-3-furanyl]-5-heptenoic acid

Following the procedure of Example 38 except substituting 1-(1-propenyl)thiol for 1-hexanethiol, the title compound is obtained.

EXAMPLE 51

(3α,4α)-7-[4-[2-(Hexyloxy)ethyl]tetrahydro-3-furanyl]-heptanoic acid

Following the procedure of Example 37 except substituting the Example 21 Part B aldehyde for the Example 1 Part A (16) aldehyde used in Example 37 Part A, the title compound is obtained.

EXAMPLE 52

(3α,4α)-7-[4-[2-(Cyclopentylethyloxy)ethyl]tetrahydro-3-furanyl]heptanoic acid

Following the procedure of Example 37 except substituting the Example 21 Part B aldehyde for the Example 1 Part A (16) aldehyde used in Example 37 Part A and substituting cyclopentylethyl mesylate for hexyl mesylate, the title compound is obtained.

EXAMPLE 53

(3α,4α)-7-[4-[2-(benzyloxy)ethyl]tetrahydro-3-furanyl]-heptanoic acid

Following the procedure of Example 37 except substituting the Example 21 Part B aldehyde for the Example 1 Part A (16) aldehyde used in Example 37 Part A and substituting benzyl mesylate for hexyl mesylate, the title compound is obtained.

EXAMPLE 54

(3α,4α)-7-[4-[2-(Phenyloxy)ethyl]tetrahydro-3-furanyl]-5-heptenoic acid

Following the procedure of Examples 37 and 6 except substituting the Example 21 Part B aldehyde for the Example 1 Part A (16) aldehyde used in Example 37 Part A and substituting the resulting (3α,4α)-7-[4-[2-(hydroxyethyl)]tetrahydro-3-furanyl]heptanoic acid, methyl ester for Example 1 Part B alcohol in Example 6 Part (a), the title acid is obtained.

EXAMPLE 55

(3α,4α)-7-[4-[2-(Cyclopentyloxy)ethyl]tetrahydro-3-furanyl]heptanoic acid

Following the procedure of Example 37 except substituting the Example 21 Part B aldehyde for the Example 1 Part A (16) aldehyde used in Example 37 Part A and substituting cyclopentyl mesylate for hexyl mesylate, the title compound is obtained.

EXAMPLE 56

(3α,4α)-7-[4-[2-(3-Hexenyloxy)ethyl]tetrahydro-3-furanyl]heptanoic acid

Following the procedure of Example 37 except substituting the Example 21 Part B aldehyde for the Example 1 Part A (16) aldehyde used in Example 37 Part A and substituting 3-hexenyl mesylate for hexyl mesylate, the title compound is obtained.

EXAMPLE 57

(3α,4α)-7-[4-[2-(Cyclopropylmethylthio)ethyl]tetrahydro-3-furanyl]heptanoic acid Following the procedure of Example 38 except substituting the Example 21 Part B aldehyde for the Example 37 Part A aldehyde and substituting cyclopropylmethyl mercaptan for 1-hexanethiol, the title compound is obtained.

EXAMPLE 58

(3α,4α)-7-[4-[2-(Benzylthio)ethyl]tetrahydro-3-furanyl]heptanoic acid

Following the procedure of Example 38 except substituting the Example 21 Part B aldehyde for the Example 37 Part A aldehyde and substituting benzylmercaptan for 1-hexanethiol, the title compound is obtained.

EXAMPLE 59

(3α,4α)-7-[4-[2-(Phenylthio)ethyl]tetrahydro-3-furanyl]heptanoic acid

Following the procedure of Example 38 except substituting the Example 21 Part B aldehyde for the Example 37 Part A aldehyde and substituting phenylmercaptan for 1-hexanethiol, the title compound is obtained.

EXAMPLE 60

(3α,4α)-7-[4-[2-(Cyclohexylthio)ethyl]tetrahydro-3-furanyl]heptanoic acid

Following the procedure of Example 38 except substituting the Example 21 Part B aldehyde for the Example 37 Part A aldehyde and substituting cyclohexylmercaptan for 1-hexanethiol, the title compound is obtained.

EXAMPLE 61

(3α,4α)-7-[4-[2-(2-Heptenylthio)ethyl]tetrahydro-3-furanyl]heptanoic acid

Following the procedure of Example 38 except substituting the Example 21 Part B aldehyde for the Example 37 Part A aldehyde and substituting 1-(2-heptenyl)-thiol for 1-hexanethiol, the title compound is obtained.

EXAMPLE 62

[3α(Z),4α]-7-[4-[4-(Hexyloxy)butyl]tetrahydro-3-furanyl]-5-heptenoic acid

A.

[3α(Z),4α]-7-[4-[3-(3-Oxo)propyl]tetrahydro-3-furanyl]-5-heptenoic acid, methyl ester Following the procedure of Example 37 Part A except substituting [3α(Z),4α]-7-[4-[2-(2-oxo)ethyl]tetrahydro-3-furanyl]-5-heptenoic acid, methyl ester for [3α(Z),4α]-7-[(4-formyl)tetrahydro-3-furanyl]-5-heptenoic acid, methyl ester, the title A compound is obtained.

B.

[3α(Z),4α]-7-[4-(4-Oxo)butyl]tetrahydro-3-furanyl]-5-heptenoic acid, methyl ester Following the procedure of Example 37 Part A except substituting the aldehyde from Part A above for [3α(Z),4α]-7-[4-[2-(2-oxo)ethyl]tetrahydro-3-furanyl]-5-heptenoic acid, methyl ester, the title B aldehyde is obtained.

C.

[3α(Z),4α]-7-[4-(4-Hydroxybutyl)]tetrahydro-3-furanyl]-5-heptenoic acid, methyl ester Following the procedure of Example 37 Part B except substituting the title B aldehyde for [3α(Z),4α]-7-[4-[2-(2-oxo)ethyl]tetrahydro-3-furanyl]-5-heptenoic acid, methyl ester, the title C alcohol is obtained.

D.

[3α(Z),4α]-7-[4-[4-(Hexyloxy)butyltetrahydro-3-furanyl]-5-heptenoic acid

Following the procedure of Example 1 except substituting the above part C alcohol for the alcohol used in Example 1 Part C, the title compound is obtained.

EXAMPLE 63

[3α(Z),4α]-7-[4-[4-(Benzyloxy)butyl]tetrahydro-3-furanyl]-5-heptenoic acid

Following the procedure of Examples 62 and 37 except substituting the Example 62 Part C alcohol for the Example 37 Part A alcohol and substituting benzyl mesylate for hexyl mesylate, the title compound is obtained.

EXAMPLE 64

[3α(Z),4α]-7-[4-[4-(Cyclohexylthio)butyl]tetrahydro-3-furanyl]-5-heptenoic acid

Following the procedure of Examples 62, 37 and 38 except substituting the Example 62 Part C alcohol for the Example 37 Part B alcohol and substituting cyclohexylmercaptan for 1-hexanethiol, the title compound is obtained.

EXAMPLE 65

[3α(Z),4α]-7-[4-[(Hexylsulfinyl)methyl]tetrahydro-3-furanyl]-5-heptenoic acid and

[3α(Z),4α]-7-[4-(Hexylsulfonyl)methyl]tetrahydro-3-furanyl]-5-heptenoic acid

To a solution of 562 mg (1.72 mmol) of [3α(Z),4α]-7-[4-[(hexylthio)methyl]tetrahydro-3-furanyl]-5-heptenoic acid, methyl ester (prepared as described in Example 4) in 6.78 ml of methanol at 0° C. is added dropwise over 4 minutes 8.37 ml of 0.5M aqueous sodium periodate solution. Tetrahydrofuran (2 ml) is then added and the resulting reaction mixture is stirred at room temperature for 15 hours. A white precipitate is removed by filtration and washed with ether (3×50 ml). The filtrate is washed with 60 ml of saturated aqueous NaHCO$_3$ solution and dried over anhydrous magnesium sulfate. Concentration in vacuo affords 539 mg of an oily crude product. This is chromatographed on 54.16 g of silica gel 60 using 0.5–1.0% CH$_3$OH to give the title compounds.

EXAMPLE 66

[3α(Z),4α]-7-[4-[(Hexylsulfonyl)methyl]tetrahydro-3-furanyl]-5-heptenoic acid

To a stirred solution of 143 mg (0.4 mmol) of the Example 65 sulfonyl compound in 20.3 ml of THF and 3.09 ml of H$_2$O under argon is added 3.90 ml of 1N aqueous lithium hydroxide solution. This mixture is purged with argon vigorously for 10 minutes and stirred at room temperature for 6 hours. The reaction mixture is acidified to pH 4 by addition of 1N aqueous HCl solution and poured into 30 ml of saturated NaCl solution. The resulting solution is saturated with solid NaCl and extracted with EtOAc (4×50 ml). The combined EtOAc extracts are dried (MgSO$_4$), filtered and concentrated in vacuo to give 140 mg of crude acid which is purified by flash chromatography.

EXAMPLE 67

[3α(Z),4α]-7-[4-[(Hexylsulfinyl)methyl]tetrahydro-3-furanyl]-5-heptenoic acid

To a stirred solution of 120 mg (0.35 mmol) of Example 65 ester and sulfinyl ester in 27.0 ml of THF and 4.11 ml of H$_2$O under argon is added 5.19 ml of 1N aqueous lithium hydroxide solution. This mixture is purged with argon vigorously for 10 minutes and stirred at room temperature for 6 hours. The reaction mixture is acidified to pH 4 by addition of 1N aqueous HCl solution and poured into 50 ml of saturated NaCl solution. The resulting solution is saturated with solid NaCl and extracted with EtOAc (4×100 ml). The combined EtOAcextracts are dried (MgSO$_4$), filtered and concentrated in vacuo to give crude acid which is purified by flash chromatography.

EXAMPLE 68

[3α(Z),4β]-7-[4-[2-(Hexyloxymethyl)]tetrahydro-3-furanyl]-2,5-heptadienoic acid

A.

[3α(Z),4β]-7-[4-[2-(Hexyloxymethyl)]tetrahydro-3-furanyl]-2-selenophenyl-5-heptenoic acid, methyl ester To a solution of 308 μl of diisopropylamine (2.2 mmole) in 5 ml of dry THF, cooled at −78° C., is added dropwise 1.25 ml of a 1.6M solution of n-butyllithium in hexane. After 30 minutes at −78° C., a solution of 356 mg of [3α(Z),4β]-7-[4-[(hexyloxy)methyl]tetrahydro-3-furanyl]-5-heptenoic acid, hexyl ester, prepared as described in Example 2, (1 mmole) in 2 ml of dry THF is added dropwise. The reaction mixture is stirred for 30 minutes, whereupon a solution of 625 mg of diphenyldiselenide (2 mmole) in 2 ml of dry THF is added. The yellow color of diselenide disappears immediately upon its addition, initially. The yellow solution is stirred at −78° C. for 30 minutes, whereupon the cooling bath was removed. The reaction mixture is then quenched by addition of aqueous ammonium chloride solution. It is then diluted with water and the organic layer is separated. The aqueous layer is extracted with ether. The combined organic extract is dried over anhydrous magnesium sulfate and concentrated in vacuo. Purification by chromatography on a silica gel column and eluting with 5–25% ethyl acetate in hexane gives 600 mg of title α-selenophenyl ester (90% yield).

B.

[3α(Z),4β]-7-[4-[2-(Hexyloxymethyl)]tetrahydro-3-furanyl]-2-selenophenyl-5-heptenoic acid A solution of 600 mg of title A α-selenophenyl esters in 10 ml of distilled THF is treated with 5 ml of a 1N aqueous lithium hydroxide solution. After stirring at room temperature for 2 days, the reaction mixture is acidified with 1N aqueous hydrochloric acid solution and extracted with methylene chloride. The methylene chloride extract is dried over anhydrous magnesium sulfate and concentrated in vacuo to yield 560 mg of title acid.

C.

[3α(Z),4β]-7-[4-[2-(Hexyloxymethyl)]tetrahydro-3-furanyl]-2,5-heptadienoic acid

A solution of 560 mg of title B acid (0.86 mmole) in 10 ml of distilled THF is treated with 500 ml of a 30% aqueous hydrogen peroxide solution at 0°–5° C. After a few minutes, the cooling bath is removed and the reaction mixture is stirred at room temperature for 1 hour. It is then diluted with methylene chloride and washed thoroughly with water. The organic layer is dried over anhydrous MgSO$_4$ and concentrated under reduced pressure. The crude residue is chromatographed on a CC-7 silica gel column and eluted with 20–60% ethyl acetate in hexane to obtain the title α,β-unsaturated acid.

EXAMPLE 69

[3α(Z),4α]-7-[4-[2-(Hexylthio)methyl]tetrahydro-3-furanyl]-2,5-heptadienoic acid Following the procedure of Example 68 except substituting the Example 4 compound for the Example 2 compound in Example 68 Part A, the title compound is obtained.

EXAMPLE 70

[3α(Z),4α]-7-[4-[2-(Phenyloxy)methyl]tetrahydro-3-furanyl]-2,5-heptadienoic acid Following the procedure of Example 68 except substituting the ester compound prepared in Example 6 for the Example 2 compound in Example 68, Part A, the title compound is obtained.

EXAMPLE 71

[3α(Z),4α]-7-[4-[2-(Benzyloxy)methyl]tetrahydro-3-furanyl]-2,5-heptadienoic acid Following the procedure of Example 68 except substituting the ester compound prepared in Example 7 for the Example 2 compound in Example 68 Part A, the title compound is obtained.

EXAMPLE 72

[3α(Z),4α]-7-[4-[(2-Pentenyloxy)methyl]tetrahydro-3-furanyl]-2,5-heptadienoic acid Following the procedure of Example 68 except substituting the ester compound prepared in Example 9 for the Example 2 compound in Example 68 Part A, the title compound is obtained.

EXAMPLE 73

[3α(Z),4α]-7-[4-[(Heptyloxy)methyl)]tetrahydro-3-furanyl]-2,5-heptadienoic acid

Following the procedure of Example 68 except substituting the ester compound prepared in Example 11 for the Example 2 compound in Example 68 Part A, the title compound is obtained.

EXAMPLE 74

[3α(Z),4α]-7-[4-[(Cyclopentyloxy)methyl]tetrahydro-3-furanyl]-2,5-heptadienoic acid Following the procedure of Example 68 except substituting the ester compound prepared in Example 13 for the Example 2 compound in Example 23 Part A, the title compound is obtained.

EXAMPLE 75

[3α(Z),4β]-7-[4-[(Cyclohexyloxy)methyl]tetrahydro-3-furanyl]-2,5-heptadienoic acid Following the procedure of Example 68 except substituting the ester compound prepared in Example 14 for the Example 2 compound in Example 68 Part A, the title compound is obtained.

EXAMPLE 76

[3α(Z),4β]-7-[4-[(3-Butenyloxy)methyl]tetrahydro-3-furanyl]-2,5-heptadienoic acid Following the procedure of Example 68 except substituting the ester compound prepared in Example 15 for the Example 2 compound in Example 68 Part A, the title compound is obtained.

EXAMPLE 77

[3α(Z),4α]-7-[4-[(2-Hexenylthio)methyl]tetrahydro-3-furanyl]-2,5-heptadienoic acid Following the procedure of Example 68 except substituting the ester compound prepared in Example 16 for the Example 2 compound in Example 68 Part A, the title compound is obtained.

EXAMPLE 78

(3α,4α)-7-[4-[(Hexyloxy)methyl)]tetrahydro-3-furanyl]-2,5-heptadienoic acid

Following the procedure of Example 68 except substituting the ester compound prepared in Example 21 for the Example 2 compound in Example 68 Part A, the title compound is obtained.

EXAMPLE 79

(3α,4α)-7-[4-[(Octylthio)methyl]tetrahydro-3-furanyl]-2-heptenoic acid

Following the procedure of Example 68 except substituting the ester compound prepared in Example 31 for the Example 2 compound in Example 68 Part A, the title compound is obtained.

EXAMPLE 80

[3α(Z),4α]-7-[4-[2-(Hexyloxy)ethyl]tetrahydro-3-furanyl]-2,5-heptadienoic acid

Following the procedure of Example 68 except substituting the ester compound prepared in Example 37 for the Example 2 compound in Example 68 Part A, the title compound is obtained.

EXAMPLE 81

[3α(Z),4α]-7-[4-[2-(Hexylthio)ethyl]tetrahydro-3-furanyl]-2,5-heptadienoic acid

Following the procedure of Example 68 except substituting the ester compound prepared in Example 38 for the Example 2 compound in Example 68 Part A, the title compound is obtained.

EXAMPLE 82

(3α,4α)-7-[4-[2-(Hexyloxy)ethyl]tetrahydro-3-furanyl]-2-heptenoic acid

Following the procedure of Example 68 except substituting the ester compound prepared in Example 51 for the Example 1 compound in Example 68 Part A, the title compound is obtained.

EXAMPLE 83

(3α,4α)-7-[4-[2-(Cyclohexylthio)ethyl]tetrahydro-3-furanyl]-2-heptenoic acid

Following the procedure of Example 68 except substituting the ester compound prepared in Example 60 for the Example 1 compound in Example 68 Part A, the title compound is obtained.

EXAMPLES 84 TO 93

Following the procedure as outlined in the specification and described in the working Examples, the following additional compounds may be prepared.

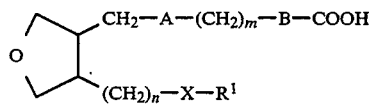

| Ex. No. | A | m | B | $(CH_2)_n$ | $R^1$ | X |
|---|---|---|---|---|---|---|
| 84. | CH=CH | 1 | CH=CH | $CH_2$ | $CH_3CH=CH$ | S |
| 85. | $(CH_2)_2$ | 2 | CH=CH | $(CH_2)_2$ | $CH_3CH_2CH=CHCH_2-$ | O |
| 86. | — | 3 | CH=CH | $(CH_2)_3$ | cyclopentyl | $\overset{\overset{\displaystyle O}{\|}}{\underset{\underset{\displaystyle O}{\|}}{S}}$ |
| 87. | CH=CH | 4 | — | $-\underset{\underset{\displaystyle CH_3}{\|}}{CH}CH_2-$ | cyclohexyl-$CH_2$ | $\overset{\overset{\displaystyle O}{\|}}{\underset{\underset{\displaystyle O}{\|}}{S}}$ |
| 88. | $(CH_2)_2$ | 5 | CH=CH | $(CH_2)_4$ | $C_6H_5$ | S |
| 89. | CH=CH | 6 | — | $(CH_2)_5$ | $C_6H_5(CH_2)_2$ | O |
| 90. | $\underset{\underset{\displaystyle CH_3}{\|}}{CH}-CH_2$ | 7 | — | $(CH_2)_6$ | $C_6H_5CH_2$ | S |
| 91. | $CH_2CH$ | 8 | CH=CH | $(CH_2)_7$ | $C_6H_{13}$ | $\overset{\overset{\displaystyle O}{\|}}{S}$ |
| 92. | $(CH_2)_2$ | 6 | CH=CH | $(CH_2)_8$ | $C_7H_{15}$ | $\overset{\overset{\displaystyle O}{\|}}{\underset{\underset{\displaystyle O}{\|}}{S}}$ |
| 93. | — | 2 | — | $(CH_2)_2$ | $C_2H_5$ | O |

What is claimed is:

1. A compound of the structure

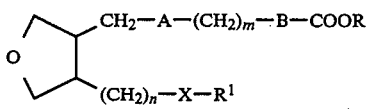

including all stereoisomers thereof, wherein A is $(CH_2)_2$, CH=CH or a single bond; B is a single bond or —CH=CH—; m is 1 to 8; n is 1 to 4; X is O or

wherein n' is 0, 1 or 2; R is H, lower alkyl or alkali metal; and $R^1$ is lower alkyl, aryl, arylalkyl, cycloalkyl, cycloalkylalkyl or lower alkenyl.

2. The compound as defined in claim 1 wherein A CH=CH and B is a single bond.

3. The compound as defined in claim 1 wherein X is O or S.

4. The compound as defined in claim 1 wherein m is 3 to 5 and n is 1.

5. The compound as defined in claim 1 wherein $R^1$ is H.

6. The compound as defined in claim 1 wherein B is a single bond, n is 1, A is CH=CH, X is O or S, n is 1, m is 3 to 5, R is H and $R^1$ is lower alkyl.

7. The compound as defined in claim 1 wherein $R^1$ is butyl, pentyl, hexyl or heptyl including all isomers thereof.

8. The compound as defined in claim 1 having the name [3α(Z),4α]-7-[4-[(hexyloxy)methyl]tetrahydro-3-furanyl]-5-heptenoic acid, including all stereoisomers thereof.

9. The compound as defined in claim 1 having the name [3α(Z),4β]-7-[4-[(hexyloxy)methyl]tetrahydro-3-furanyl]-5-heptenoic acid or the hexyl ester thereof, including all stereoisomers thereof.

10. The compound as defined in claim 1 having the name [3α(Z),4α]-7-[4-[(hexylthio)methyl]tetrahydro-3-furanyl]-5-heptenoic acid or its methyl ester including all stereoisomers thereof.

11. A method of inhibiting arachidonic acid-induced platelet aggregation and broncho-constriction, which comprises administering to the circulatory system of a mammalian host an effective amount of a compound as defined in claim 1 or a pharmaceutically acceptable salt thereof.

12. The method as defined in claim 11 wherein said compound is administered in an amount within the range of from about 1 to about 100 mg/kg.

13. A composition for inhibiting arachidonic acid-induced platelet aggregation and bronchoconstriction comprising an effective amount of a compound as defined in claim 1 or a pharmaceutically acceptable salt thereof, and a pharmaceutically acceptable carrier therefor.

14. A method of inhibiting platelet aggregation which comprises administering to a mammalian host an effective amount of a compound as defined in claim 1 or a pharmaceutically acceptable salt thereof.

15. A method of inhibiting bronchoconstriction associated with asthma, which comprises administering to a mammalian host an effective amount of a compound as defined in claim 1 or a pharmaceutically acceptable salt thereof.

16. A method for treating peripheral vascular disease, which comprises topically or systemically administering to a mammalian host an effective amount of a compound as defined in claim 1 or a pharmaceutically acceptable salt thereof.

17. A method for inhibiting platelet aggregation and bronchoconstriction by inhibiting production of thromboxane $A_2$ by blocking the action of thromboxane synthetase, which comprises administering to a mammalian host an effective amount of a compound as defined in claim 1 or a pharmaceutically acceptable salt thereof.

18. A method for treating inflammation in a mammalian species in need of such treatment, which comprises administering to a mammalian host an effective amount of a compound as defined in claim 1 or a pharmaceutically acceptable salt thereof.

19. A method of relieving pain in a mammalian specie, which comprises administering to said mammalian specie a composition containing an analgesically effective amount of a compound as defined in claim 1 or a pharmaceutically acceptable salt thereof.

* * * * *

UNITED STATES PATENT AND TRADEMARK OFFICE
CERTIFICATE OF CORRECTION

PATENT NO. : 4,521,539
DATED : June 4, 1985
INVENTOR(S) : Jagabandhu Das

It is certified that error appears in the above—identified patent and that said Letters Patent is hereby corrected as shown below:

Column 2, after the first structure, replace the comma with a period.
Column 6, line 35, "witting" should read --Wittig--.
Column 6, structure XIV should read -- 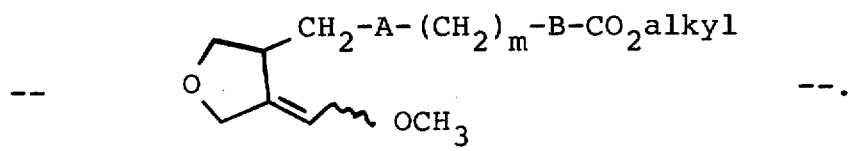 --.

Column 7, line 30, "either" should read --ether--.
Column 9, structure F should read -- 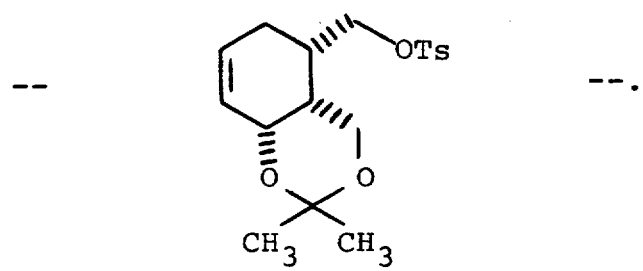 --.

Column 23, lines 21 and 24, "(3α,4α)" should read --(3α,4β)--.

Signed and Sealed this

Twenty-second Day of October 1985

[SEAL]

Attest:

DONALD J. QUIGG

Attesting Officer

Commissioner of Patents and Trademarks—Designate